(12) United States Patent
Ramanathan et al.

(10) Patent No.: US 6,723,887 B2
(45) Date of Patent: Apr. 20, 2004

(54) PROCESS FOR THE PRODUCTION OF DIFLUOROMETHANE

(75) Inventors: Rajasekaran Ramanathan, New Delhi (IN); Rajdeep Anand, New Delhi (IN); Anurag Jain, New Delhi (IN); Jampani Madhusudana Rao, Andhra Pradesh (IN)

(73) Assignee: SFR Limited, New Delhi (IN)

( * ) Notice: Subject to any disclaimer, the term of this patent is extended or adjusted under 35 U.S.C. 154(b) by 0 days.

(21) Appl. No.: 10/193,936

(22) Filed: Jul. 12, 2002

(65) Prior Publication Data
US 2004/0010168 A1 Jan. 15, 2004

(51) Int. Cl.$^7$ .......................... C07C 17/00; C07C 17/08; C07C 19/08
(52) U.S. Cl. ................. 570/169; 570/165; 570/166; 570/167; 570/168
(58) Field of Search ............................ 570/169, 165, 570/168, 167, 166

(56) References Cited

U.S. PATENT DOCUMENTS 5,763,708 A * 6/1998 Clemmer et al. ........... 570/169
6,242,659 B1 * 6/2001 Requieme et al. .......... 570/169

* cited by examiner

Primary Examiner—Johann Richter
Assistant Examiner—Elvis O. Price
(74) Attorney, Agent, or Firm—Schweitzer Cornman Gross & Bondell LLP

(57) ABSTRACT

A process for vapor phase fluorination of methylene chloride with anhydrous hydrogen fluoride (AHF) in the presence of a coprecipitated chromia-alumina impregnated with zinc salt as catalyst, removing HCl and heavier components by distillation, subjecting HFC-32 rich cut to a further step of fluorination in the presence of a fluorination catalyst.

11 Claims, 3 Drawing Sheets

PROCESS FOR THE PRODUCTION OF DIFLUOROMETHANE

FIELD OF THE INVENTION

This invention relates to a process for the preparation of difluoromethane (HFC-32) by vapor phase fluorination of methylene chloride with anhydrous hydrogen fluoride (AHF) using a coprecipitated chromia-alumina impregnated with a zinc salt as catalyst and purification of difluoromethane thus obtained, after removal of HCl and heavier components for enhancing the forward reaction of HCFC-31 to HFC-32, is passed over the fluorination catalyst in a second reactor to reduce the concentration of chlorofluoromethane (HCFC-31) by converting to pure HFC-32.

BACKGROUND OF THE INVENTION

Hydrochlorofluorocarbons and Chlorofluorocarbons are used, extensively, as foam blowing agents, refrigerants, cleaning solvents and propellants for aerosol sprays. However, in the recent years there has been increasing international concern that chlorofluorocarbons may be damaging the earth's protective ozone layer, which helps in containing the UV rays coming to earth. To this effect an international legislation has been put in place to ensure that their manufacture/use is phased out, completely. Extensive research work is being done to take care of the said concern and efforts are on to find suitable replacement(s) for chlorofluorocarbons. One such replacement could be fluorocarbons which do not contain chlorine, but which contain hydrogen.

The hydrofluorocarbon difluoromethane (HFC-32) is of interest as a substitute by itself or in the form of a blend with other hydrofluoroalkanes like 1,1,1,2-tetrafluoroethane (HFC-134a) and pentafluoraethane (HFC-125) for substituting ozone depleting HCFC's like chlorodifluoromethane (R-22) and R-502 in refrigeration, air-conditioning and other applications.

PRIOR ART

It is known in the art that the catalytic vapor phase fluorination of haloalkanes containing at least one halogen atom selected from chlorine or bromine in the molecule with hydrogen fluoride results in the formation of fluorine rich haloalkanes. In the early stages aluminium fluoride and chromium fluoride were found suitable as catalysts for vapour phase fluorination of haloalkanes.

One of the earliest patent, U.S. Pat. No. 2,744,148, disclosed a metal halide of elements selected from nickel, chromium, cobalt, copper or palladium carried on aluminium fluoride as catalyst for fluorination of methylene chloride. However, the yield of HFC-32 was only 15%. The use of an oxygenated chromium trifluoride disclosed in U.S. Pat. No. 2,745,886 gave an yield of 35.7%.

The fluorination of methylene chloride to give HFC-32 involves two reaction steps. The first step is the exchange of one chlorine in dichloromethane by fluorine to give chrofluoromethane (HCFC-31). In the second step HCFC-31 is further fluorinated to give HFC-32. Both the steps referred above are reversible. All subsequent efforts were directed to the development of the fluorination catalyst that gave high conversion of methylene chloride with high selectivity of HFC-32.

UK patent GB 1307224 teaches the preparation of a chromium oxide catalyst for use in fluorination reaction. The examples carried out with methylene chloride and HF at 320° C. gave a conversion of 51.7% and selectivity of 63.8% for HFC-32. The U.S. Pat. Nos. 6,337,299 and 6,300,531 reports use of chromium oxide as a fluorination catalyst for methylene chloride conversion to HFC-32. A conversion of 62% and selectivity of 80% for HFC-32 was reported. The U.S. Pat. No. 5,569,795 utilising chromia based, U.S. Pat. No. 5,900,514 utilising bulk chromia, U.S. Pat. No. 6,242,659 utilising chromium oxide with nickel and U.S. Pat. No. 5,763,704 utilising co-precipitated chromium oxide and Zinc as fluorination catalyst for the conversion of methylene chloride to HFC-32 is known. The highest conversion and selectivity of 99% and 93%, respectively were reported in U.S. Pat. No. 5,763,704 using $Zn/Cr_2O_3$ catalyst. However this was achieved only when the mole ratio of HF to methylene chloride was as high as 27.

The U.S. Pat. No. 5,710,353 reports the use of alumina or compounds of the element selected from Ti, V, Zr, Ge, Sn, Mo and Pb on alumina for the preparation of fluorination catalyst. This patent reports a very low conversion of 16.4% and a selectivity of 46.3% for HFC-32 using alumina alone. But the co-precipitated $TiO_2/Al_2O_3$ gave a conversion of 75.7% and selectivity of 82% at a high mole ratio of HF to methylene chloride of about 17.

EP Patent 0128510 reports the use of aluminium chloride or alumina or mixed halide of chromia and alumina or mixed oxides of chromia and alumina or ferric chloride on carbon to generate catalysts for the fluorination of methylene chloride to HFC-32. The highest conversion of methylene chloride reported was 93% with 82% selectivity for HFC-32.

U.S. Pat. Nos. 5,155,082 and 5,763,708 report the use of a mixed oxide catalyst comprising $CrO_3/Al_2O_3$ for the fluorination of methylene chloride to give HFC-32. The conversion and selectivity obtained was 82% and 89% in U.S. Pat. No. 5,763,708. EP 0805136 discloses a fluorination catalyst prepared by chromium and nickel compounds on aluminium fluoride for the fluorination of methylene chloride to HFC-32 to obtain a 61% conversion of methylene chloride and selectivity of 96% for HFC-32.

A serious problem with the production of difluoromethane by the fluorination of dichloromethane is that a substantial amount of a highly toxic intermediate, chlorofluoromethane (HCFC 31), is produced as an impurity.

To address this impurity, the conventional distillation process is of little help despite the difference in relative volatility between HCFC-31 (b.p. −9.1 degree. C.) and HCFC-32 (b.p.: −51.7 degree C.) to bring down HCFC-31 below permissible limits.

European patent application EP 0508 630 describes a process for the contact of HFC-32 with an activated carbon to lower the HCFC-31 impurity in HFC-32. However, in the process, the selectivity is not very high and difluoromethane is adsorbed in the same proportions as HCFC-31, which in turn takes away the useful product as well as exhausts the capacity of the adsorbent at a faster rate than desired.

The use of molecular sieves for the purification of fluorohydrocarbons is known in the art. The purification treatments are usually performed at around ambient temperature. A process has been described in U.S. Pat. No. 5,608,129, to remove the traces of HCFC-31 present in HFC-32 by passing over a 13×molecular sieve at a temperature of at least 60 degree C.

An article by Rao, J. M. et al [See J. M. Rao et al Journal of Fluorine Chemistry 95 (1999) 177–180] teaches a process for preparing a catalyst based on co-precipitated chromia-alumina doped with zinc and/or magnesium involving the steps of co-precipitating chromia and alumina, washing and drying, shaping and impregnation of zinc chloride. The article also explains the occurrence of dismutation reaction in catalytical vapor phase halogen exchange reaction, which was attributed to the presence of strong acid centres in the catalyst. PCT application no. WO 01/74483 also mentions coprecipitated catalyst promoted with zinc.

SUMMARY OF THE INVENTION

The main object of the present invention is to provide a process for the preparation of difluoromethane and minimize the quantity of HCFC-31 in the product stream.

The coprecipitated chromia-alumina with zinc salt catalyst, when employed for the fluorination of methylene chloride, exhibited higher conversion and higher selectivity for HFC-32 under specific process conditions and also minimising formation of side products like methyl chloride and chloroform. The invention also embodies the reduction in the relative percentage of strong acid sites in the catalyst in order to achieve high selectivity.

The present invention relates to a process for the preparation of difluoromethane (HFC-32) by vapor phase fluorination of methylene chloride with anhydrous hydrogen fluoride (AHF) in the presence of a coprecipitated chromia-alumina impregnated with zinc salt as catalyst at a temperature ranging from 225–375° C., preferably 250 to 350° C., more preferably 260–325° C. and contact time not exceeding 20 seconds, preferably between 4 to 10 seconds, removing HCl and heavier components by distillation, subjecting HFC 32 rich cut to a further step of fluorination in presence of fluorination catalyst to convert chlorofluroromethane (HCFC-31), an intermediate formed along with HFC-32, to HFC-32 thereby reducing the concentration of HCFC 31 in HFC-32 rich cut to obtain pure HFC-32.

In another embodiment of the invention the molar ratio of methylene chloride anhydrous hydrogen fluoride is in the range of 1:2.1 to 1:15, preferably in the range of 1:2.5 to 1:6.

Further, according to the present invention, the intermediate HCFC-31 present as an impurity in HFC-32, coming out of the reaction section and after HCl and heavier components removal is converted to HFC-32 by passing over fluorination catalyst in the second reactor to fluorinate HCFC-31 to HFC-32.

In another embodiment of the invention the highly toxic HCFC-31 is converted into the desired HFC-32 therein minimising the interaction of HCFC-31 with the environment substantially.

In another embodiment the heavier components comprising HCFC-31, unreacted methylene chloride and HF obtained after distillation of effluent stream coming out of the reactor is recycled back to the original feed.

DETAILED DESCRIPTION OF THE INVENTION

The present invention is to provide a process for the preparation of difluoromethane and minimize the quantity of HCFC-31 in the product stream. Further, this product stream is distilled to obtain an HFC-32 rich stream which contains HCFC-31 and HF This stream is passed in the second reactor over a fluorination catalyst to get pure HFC-32.

The catalyst comprising a co-precipitated chromia alumina impregnated with a zinc salt, when employed for the fluorination of methylene chloride exhibited higher conversion and higher selectivity for HFC-32 and also minimising formation of side products like methyl chloride and chloroform. The said catalyst is used to convert the HCFC-31 present in the product stream to HFC-32.

The present invention relates to a process for the reaction of methylene chloride with anhydrous HF in the presence of said catalyst which provides higher conversion of methylene chloride with high selectivity for HFC-32 and also convert HCFC-31 present in the product stream to HFC-32.

The basic factors that influence the conversion of methylene chloride and selectivity for HFC-32 are:
Reaction temperatures
Mole ratio of methylehe chloride to AHF
The contact time for reaction
The characteristics of the precatalyst
The activation of precatalyst with HF.

The co-precipitated chromia alumina catalyst contain chromium-aluminium in the atomic ratio 1:1 to 1:10 and the amount of zinc compound used for impregnation of co-precipitated Chromia/Alumina catalyst ranges from 3–11% by weight. The catalyst should be X-ray amorphous and should contain the alumina in gamma phase and the chromia as chromium oxide trihydrate. The oxidation state of Cr should preferably be Cr (III) and the wt. % of Cr (VI) should be in the range 0–2% of the total chromium present in the said catalyst.

The fluorination reaction is carried out at a temperature in the range of 225–375° C. The reaction temperature should preferably be in the range 250–350° C. and more preferably between 260–325° C.

The fluorination of methylene chloride with AHF using the co-precipitated chromia-alumina with zinc salt as catalyst to give HFC-32 could be carried out at pressures in the range from sub-atmospheric to superatmospheric pressures. The fluorination using the catalyst under the above mentioned temperature conditions is carried out at superatmospheric pressures.

The stoichiometric ratios for the fluorination of methylene chloride with HF is 1:2. However, excess of HF contributes to higher conversions and also extends the life of the said catalyst. The present invention uses excess of AHF and the mol. ratio of methylene chloride to AHF is in the range of 1:2.1 to 1:15, preferably, in the range 1:2.5 to 1:6.

The contact time for the fluorination of methylene chloride using AHF and the coprocitated chromia alumina with zinc salt as catalyst is in the range 3–20 seconds, preferably, in the range of 4–10 seconds.

The catalytic activity in the halogen exchange has been attributed to the Lewis acid centers. In the case of chromia based catalyst the activity was attributed to the number of reversibly oxidizable sites in the precatalyst. In the alumina based catalyst the formation of AlF3 in the beta and gamma phase during activation is critical to the catalytical activity. The activation of precatalyst is carried out under controlled conditions preventing the formation of alpha aluminium fluoride and the amorphous nature of the catalyst is maintained.

The catalyst was calcined and further activated by treating sequentially with $N_2$ at 400° C. for 24 hours followed by fluorination in the temperature range 150° to 400° C. till the exit stream of HF contains less that 1% of moisture.

The production of HFC-32 is carried out by reacting methylene chloride and HF in the presence of a co-precipitated chromia-alumina promoted with zinc salt. The effluent stream coming out of the fluorination reactor comprising of HFC-32, HCl, HCFC-31, unreacted methylene chloride and HF is sent to a second reactor. The separation and purification of HFC-32 is done in a phased manner using a series of distillations/condensations.

In another embodiment of the invention HFC-32 is purified by reacting HCFC-31, an intermediate and present as an impurity, with HF in the presence of the said catalyst. The present invention utilises the principle of enhancing the forward reaction by selectively removing one of the products formed, which in the present invention is HCl.

The present invention embodies the advantages of converting the highly toxic HCFC-31 into the desired HFC-32 therein minimising the interaction of HCFC-31 with the environment substantially.

A more complete appreciation of the invention and the attendant advantages thereof will be more clearly understood by reference to the accompanying drawings, which are for illustrative purposes, hence the same should not be construed to restrict the scope of the invention.

Figure 1:
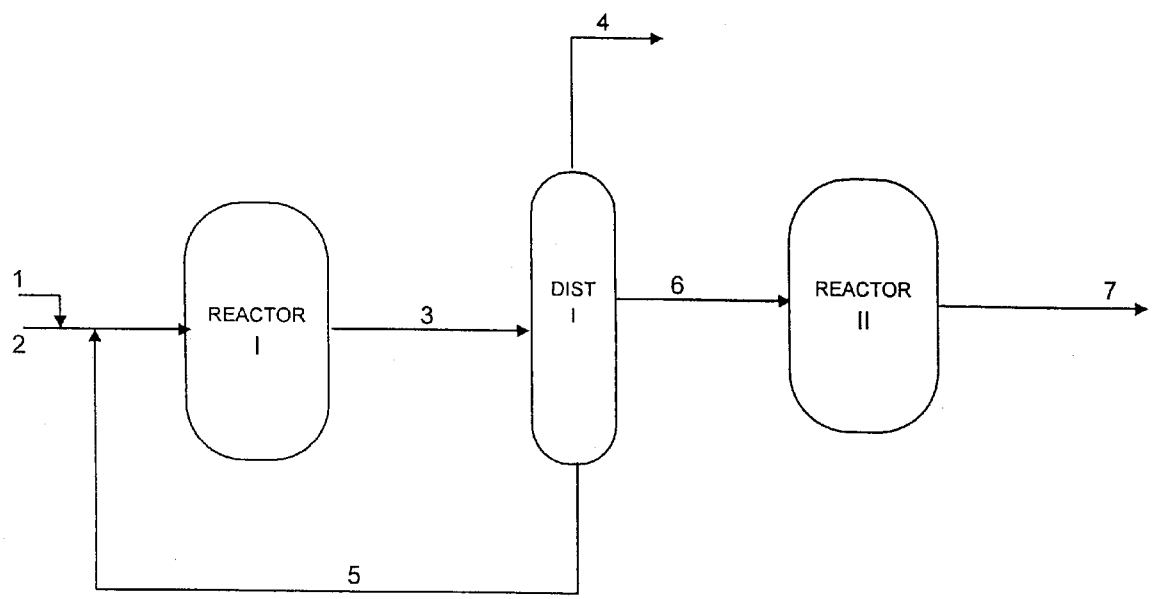
FIG. 1, is a flow sheet illustrating one embodiment of the present invention. The embodiment comprises reacting methylene chloride, process stream 2 with AHF, process stream 1 in a reactor, Reactor I to form HFC-32. The effluent stream from the reactor, process stream 3 is fed into a distillation column, Dist I to give distillate as HCl, process stream 4, and a side-cut fraction, process stream 6, containing HFC-32 as a distillate with small amounts of HCFC-31 and azeotropic HF. The process stream 6 is sent to further processing which comprises of a second reactor, Reactor II comprising a fluorination catalyst bed and the effluents of the second reactor, process stream 7 are neutralised and dried from which pure HFC-32 is recovered. The bottom process stream from Dist I, process stream 5, containing HCFC-31 and unreacted methylene chloride and HF is recycled back to the original feed stream, combined stream of process stream 1 and 2.

The present invention is illustrated in more detail below by reference to the following non-limiting examples. Preferred conditions are not necessarily used in the examples, which are intended to show the effect of varying the process conditions such as feed quantities, temperature, etc.

EXAMPLES

Example 1

Fluorination of Methylene Chloride 450 ml of the catalyst comprising co-precipitated chromia-alumina impregnated with zinc chloride (chemical composition—Cr:Al:Zn—22:75:3) was packed into an electrically heated Inconel tubular reactor provided with multiple temperature sensing points. The catalyst was pretreated by passing $N_2$ at about 400° C. for 24 hrs. The temperature of the catalyst bed was lowered to 100° C. and AHF was introduced along with $N_2$. The highly exothermic reaction occurring is controlled by adjusting the flowrates of $N_2$ and AHF and the temperature of the catalyst bed is not allowed to exceed 400° C. As the fluorination proceeds, $N_2$ is withdrawn and pure AHF was passed while simultaneously raising the temperature to 350° C. The activation of the catalyst is completed when the moisture content in the exit stream of AHF becomes less than 1%.

Then the temperature of the catalyst bed is brought to 275° C. after which the fluorination of methylene chloride with AHF was carried out by co-feeding the reactants comprising a mixture of methylene chloride 60 gm/h and HF 62 gm/h in vapor form over the activated catalyst. The effluent stream from the catalyst bed was scrubbed in KOH solution in a scrubber and then passed through a molecular sieve drier and condensed in a trap cooled in a dry ice-acetone bath.

The samples of the product stream were drawn after freeing from acidic components and drying and analyzed by GC and was found to be (by wt.) HFC-32 88.67%, HCFC-31 7.79% and methylene chloride 3.31% (Conversion of methylene chloride—96.5% and selectivity for HFC-32—91.9%)

Example 2

Fluorination of Methylene Chloride 450 ml of the catalyst comprising co-precipitated chromia-alumina impregnated with zinc chloride (chemical composition—Cr:Al:Zn—22:75:3) was packed into an electrically heated Inconel tubular reactor provided with multiple temperature sensing points. The catalyst was pretreated by passing $N_2$ at about 400° C. for 24 hrs. The temperature of the catalyst bed was lowered to 100° C. and AHF was introduced along with $N_2$. The highly exothermic reaction occurring is controlled by adjusting the flowrates of $N_2$ and AHF and the temperature of the catalyst bed is not allowed to exceed 400° C. As the fluorination proceeds, $N_2$ is withdrawn and pure AHF was passed while simultaneously raising the temperature to 350° C. The activation of the catalyst is completed when the moisture content in the exit stream of AHF becomes less than 1%.

Then the temperature of the catalyst bed is brought to 275° C. after which the fluorination of methylene chloride with AHF was carried out by co-feeding the reactants comprising a mixture of methylene chloride 87 gm/h and HF 79.5 gm/h over the activated catalyst. The effluent stream from the catalyst bed was scrubbed in KOH solution in a scrubber and then passed through a molecular sieve drier and condensed in a trap cooled in a dry ice-acetone bath.

The samples of the product stream were drawn after freeing from acidic components and drying and analyzed by GC and was found to be (by wt.) HFC-32 85.95%, HCFC-31 8.7% and methylene chloride 5.27% (Conversion of methylene chloride—94.73% and selectivity for HFC-32—90.7%)

Example 3
Fluorination of Methylene Chloride 450 ml of the catalyst comprising co-precipitated chromia-alumina impregnated with zinc chloride (chemical composition—Cr:Al:Zn—22:75:3) was packed into an electrically heated Inconel tubular reactor provided with multiple temperature sensing points. The catalyst was pre-treated by passing $N_2$ at about 400° C. for 24 hrs. The temperature of the catalyst bed was lowered to 100° C. and AHF was introduced along with $N_2$. The highly exothermic reaction occurring is controlled by adjusting the flowrates of $N_2$ and AHF and the temperature of the catalyst bed is not allowed to exceed 400° C. As the fluorination proceeds, $N_2$ is withdrawn and pure AHF was passed while simultaneously raising the temperature to 350° C. The activation of the catalyst is completed when the moisture content in the exit stream of AHF becomes less than 1%.

Then the temperature of the catalyst bed is brought to 250° C. after which the fluorination of methylene chloride with AHF was carried out by co-feeding the reactants comprising a mixture of methylene chloride 40 gm/h and HF 40 gm/h over the activated catalyst. The effluent stream from the catalyst bed was scrubbed in KOH solution in a scrubber and then passed through a molecular sieve drier and condensed in a trap cooled in a dry ice-acetone bath.

The samples of the product stream were drawn after freeing from acidic components and drying and analyzed by GC and was found to be (by wt.) HFC-32 79.6%, HCFC-31 8.5% and methylene chloride 11.9% (Conversion of methylene chloride—88.1% and selectivity for HFC-32—90.3%)

Example 4
Purification of HFC-32

Figure 2:
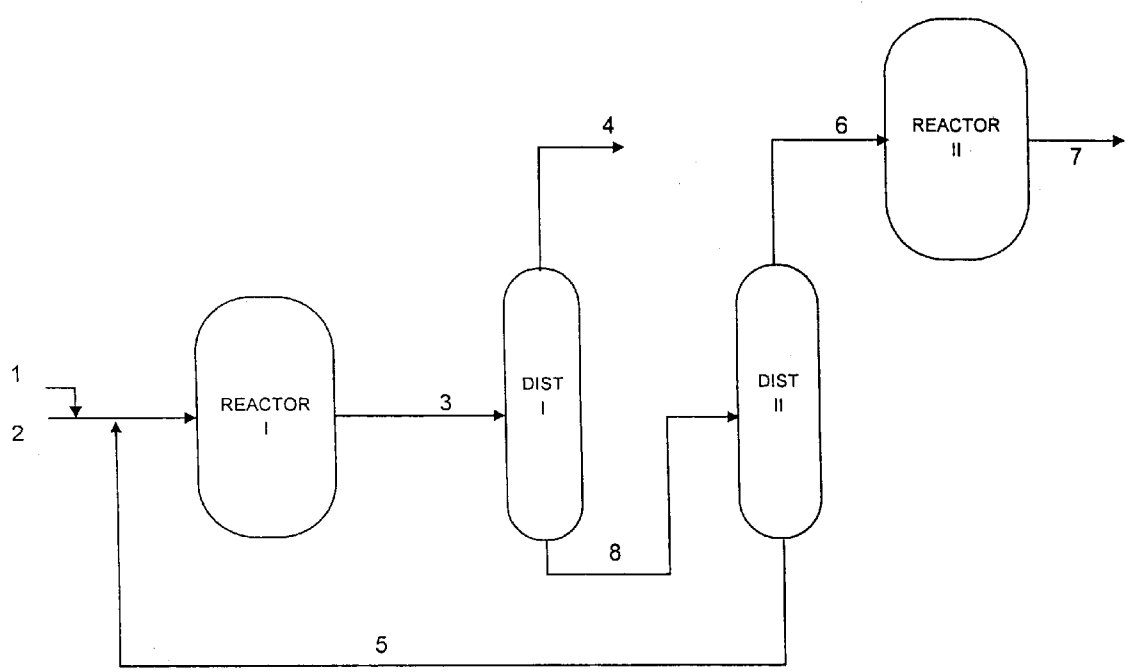
FIG. 2, is a flow sheet illustrating another embodiment in which side stream withdrawal is not employed and one additional distillation column is used. In the flow sheet illustrated in FIG. 2, feed comprising of methylene chloride, process stream 2 with AHF, process stream 1 is fed into a reactor, Reactor I to form HFC-32. The effluent stream from the reactor, process stream 3 is fed into first distillation column, Dist I to give distillate as HCl, process stream 4 and the bottom process stream 8 is fed into another distillation column, Dist II. The distillate, process stream 6 from Dist II contains HFC-32 as a main component and small amounts of HCFC-31 and azeotropic HF. The process stream 6 is sent to a second reactor, Reactor II comprising a fluorination catalyst bed. The effluents of the second reactor, process stream 7 are neutralised and dried from which pure HFC-32 is recovered. The bottom process stream from Dist II, process stream 5, containing HCFC-31 and unreacted methylene chloride and HF is recycled back to the original feed stream, combined stream of process stream 1 and 2.
Figure 3:
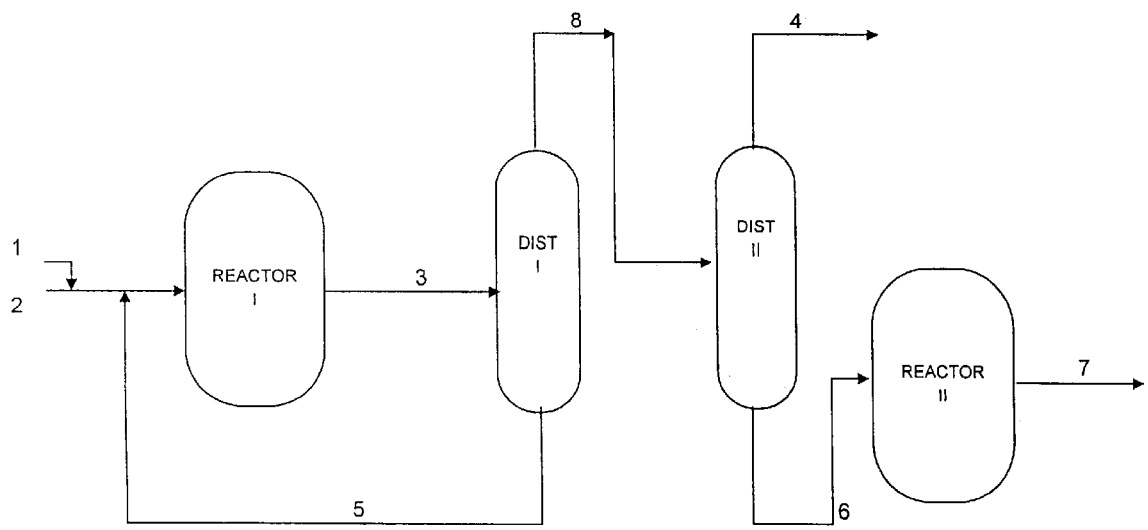
FIG. 3 is a flow sheet illustrating another embodiment in which feed comprising of methylene chloride, process stream 2 with AHF, process stream 1 is fed into a reactor, Reactor I to form HFC-32. The effluent stream from the reactor, process stream 3 is fed into first distillation column, Dist I to give distillate as HFC-32, HCl, HCFC-31 and azeotropic HF, process stream 8 and the bottom process stream 8 is fed into another distillation column, Dist II. The distillate, process stream 4 from Dist II contains HCl. The bottom of Dist II gives a process stream 6 having HFC-32 as a main component and small amounts of HCFC-31 and azeotropic HF. The process stream 6 is sent to a second reactor, Reactor II comprising a fluorination catalyst bed. The effluents of the second reactor, process stream 7 are neutralised and dried from which pure HFC-32 is recovered. The bottom process stream from Dist I, process stream 5, containing HCFC-31 and unreacted methylene chloride and HF is recycled back to the original feed stream, combined stream of process stream 1 and 2

Impure HFC-32 comprising a mixture of HFC-32 98 gm, HCFC-31 100 ppm and HF 2 gm is obtained after removal of HCl and heavier components (by any of the processes defined—FIGS. 1, 2 or 3) from the outlet stream of reactor. The mixture was fed into the reactor at 275° C. with a contact time of 12 seconds. The reactor outlet was analyzed at the sampling point for R 31 and was found to be 1 ppm.

Example 5
Purification of HFC-32

Impure HFC-32 comprising a mixture of HFC-32 98 gm, HCFC-31 100 ppm and HF 2 gm is obtained after removal of HCl and heavier components (by any of the processes defined—FIGS. 1, 2 or 3) from the outlet stream of reactor. The mixture was fed into the reactor at 275° C. with a contact time of 6 seconds. The reactor outlet was analyzed at the sampling point for R 31 and was found to be 20 ppm.

Example 6
Purification of HFC-32

Impure HFC-32 comprising a mixture of HFC-32 98 gm, HCFC-31 100 ppm and HF 2 gm is obtained after removal of HCl and heavier components (by any of the processes defined—FIGS. 1, 2 or 3) from the outlet stream of reactor. The mixture was fed into the reactor at 250° C. with a contact time of 9 seconds. The reactor outlet was analyzed at the sampling point for R 31 and was found to be 22 ppm.

Example 7
Purification of HFC-32

Impure HFC-32 comprising a mixture of HFC-32 98 gm, HCFC-31 500 ppm and HF 2 gm is obtained after removal of HCl and heavier components (by any of the processes defined—FIGS. 1, 2 or 3) from the outlet stream of reactor. The mixture was fed into the reactor at 290° C. with a contact time of 7 seconds. The reactor outlet was analyzed at the sampling point for R 31 and was found to be 56 ppm.

Example 8
Purification of HFC-32

Impure HFC-32 comprising a mixture of HFC-32 90 gm, HCFC-31 500 ppm and HF 10 gm is obtained after removal of HCl and heavier components (by any of the processes defined—FIGS. 1, 2 or 3) from the outlet stream of reactor. The mixture was fed into the reactor at 290° C. with a contact time of 9 seconds. The reactor outlet was analyzed at the sampling point for R 31 and was found to be 1 ppm.

While particular embodiments of the present invention have been illustrated and described, it would be obvious to those skilled in art that various other changes and modifications can be made without departing from the spirit and scope of the invention. It is therefore intended to cover in the appended claims all such changes and modifications that are within the scope of this invention.

What is claimed is:

1. A process for the preparation of difluoromethane (HFC-32) by vapor phase fluorination of methylene chloride with anhydrous hydrogen fluoride (AHF) in the presence of a coprecipitated chromia-alumina impregnated with zinc salt as catalyst at a temperature ranging from 225–375° C. and contact time not exceeding 20 seconds, removing HCl and heavier components by distillation, subjecting HFC-32 rich cut to a further step of fluorination in presence of fluorination catalyst to convert chlorofluoromethane HCFC-31, an intermediate formed along with HFC -32, to HFC-32 thereby reducing the concentration of HCFC 31 in HFC-32 rich cut to obtain pure HFC-32.

2. A process as claimed in claim 1, wherein the molar ratio of methylene chloride to anhydrous hydrogen fluoride is in the range of 1:2.1 to 1:15.

3. A process as claimed in claim 1, wherein the reaction is carried out at a temperature ranging from 250 to 350° C.

4. A process as claimed in claim 1, wherein the heavier components are recycled back to the original feed stream.

5. A process as claimed in claim 1, wherein the fluorination catalyst is coprecipitated chromia-alumina impregnated with zinc salt.

6. A process as claimed in claim 5, wherein the weight % of the zinc compound based on the weight of the catalyst ranges from 3–11%.

7. A process as claimed in claim 1, wherein the contact time for the fluorination of methylene chloride using AHF and the said catalyst is in the range 3–20 second.

8. A process as claimed in claim 1, wherein the molar ratio of methylene chloride to anhydrous hydrogen fluoride is in the range of 1:2.5 to 1:6.

9. A process as claimed in claim 1, wherein the reaction is carried out at a temperature ranging from 260 to 325° C.

10. A process as claimed in claim 1, wherein the contact time for the fluorination of methylene chloride ranges from 4–10 seconds.

11. The process of claim 1, wherein the coprecipitated chromia-alumina impregnated with zinc salt catalyst is first pre-heated by passing $N_2$ at elevated temperature over it.

* * * * *

UNITED STATES PATENT AND TRADEMARK OFFICE
CERTIFICATE OF CORRECTION

PATENT NO. : 6,723,887 B2
DATED : April 20, 2004
INVENTOR(S) : Rajasekaran Ramanathan et al.

It is certified that error appears in the above-identified patent and that said Letters Patent is hereby corrected as shown below:

<u>Title page,</u>
Item [73], Assignee, "SFR Limited" should read -- SRF Limited --.

Signed and Sealed this

Twenty-ninth Day of June, 2004

JON W. DUDAS
*Acting Director of the United States Patent and Trademark Office*